US010478163B2

(12) United States Patent
Prisco et al.

(10) Patent No.: US 10,478,163 B2
(45) Date of Patent: Nov. 19, 2019

(54) MEDICAL INSTRUMENT ENGAGEMENT PROCESS

(71) Applicant: Intuitive Surgical Operations, Inc., Sunnyvale, CA (US)

(72) Inventors: Giuseppe Maria Prisco, Calci (IT); Theodore W. Rogers, Alameda, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/134,836

(22) Filed: Apr. 21, 2016

(65) Prior Publication Data

US 2016/0310115 A1 Oct. 27, 2016

Related U.S. Application Data

(60) Division of application No. 13/360,395, filed on Jan. 27, 2012, now Pat. No. 9,339,342, and a continuation-in-part of application No. 12/286,644, filed on Sep. 30, 2008, now Pat. No. 9,259,274.

(60) Provisional application No. 61/485,702, filed on May 13, 2011.

(51) Int. Cl.
*A61B 17/00* (2006.01)
*A61B 34/30* (2016.01)
*A61B 34/00* (2016.01)
*A61B 46/10* (2016.01)
*A61B 34/20* (2016.01)

(52) U.S. Cl.
CPC .............. *A61B 17/00* (2013.01); *A61B 34/30* (2016.02); *A61B 34/71* (2016.02); *A61B 46/10* (2016.02); *A61B 2017/00398* (2013.01); *A61B 2017/00473* (2013.01); *A61B 2017/00477* (2013.01); *A61B 2034/2059* (2016.02)

(58) Field of Classification Search
CPC .......... A61B 17/00; A61B 2017/00017; A61B 2017/00137; A61B 2017/00389; A61B 2017/0046; A61B 2017/00464; A61B 2017/00473; A61B 2017/00477; A61B 2017/00486; A61B 34/30; A61B 34/70; A61B 34/71; A61B 34/72; A61B 34/74
USPC ....................... 606/1, 130; 128/898
See application file for complete search history.

(56) References Cited

U.S. PATENT DOCUMENTS

| | | | |
|---|---|---|---|
| 4,117,359 A | 9/1978 | Wehde | |
| 4,259,876 A | 4/1981 | Belyanin et al. | |
| 4,281,447 A | 8/1981 | Miller et al. | |
| 4,283,165 A | 8/1981 | Vertut | |
| 4,899,608 A | 2/1990 | Knappe et al. | |
| 6,007,550 A | 12/1999 | Wang et al. | |
| 6,132,368 A | 10/2000 | Cooper | |
| 6,139,245 A | 10/2000 | Hofmeister | |
| 6,331,181 B1 | 12/2001 | Tierney et al. | |
| 6,371,952 B1 | 4/2002 | Madhani et al. | |
| 6,394,998 B1 | 5/2002 | Wallace et al. | |
| 6,459,926 B1 | 10/2002 | Nowlin et al. | |
| 6,494,662 B1 | 12/2002 | De | |
| 6,817,974 B2 | 11/2004 | Cooper et al. | |
| 6,994,708 B2 | 2/2006 | Manzo | |
| 6,997,079 B2 | 2/2006 | Nomura et al. | |
| 7,048,745 B2 | 5/2006 | Tierney et al. | |
| 7,316,681 B2 | 1/2008 | Madhani et al. | |
| 7,331,967 B2 | 2/2008 | Lee et al. | |
| 7,524,320 B2 | 4/2009 | Tierney et al. | |
| 7,666,191 B2 | 2/2010 | Orban, III | |
| 7,699,855 B2 | 4/2010 | Anderson et al. | |
| 7,727,244 B2 | 6/2010 | Orban, III et al. | |
| 7,823,330 B2 | 11/2010 | Ostrowski et al. | |
| 7,886,743 B2 | 2/2011 | Cooper et al. | |
| 7,935,130 B2 | 5/2011 | Williams et al. | |
| 7,947,050 B2 | 5/2011 | Lee et al. | |
| 7,947,051 B2 | 5/2011 | Lee et al. | |
| 7,963,913 B2 | 6/2011 | Devengenzo et al. | |
| 8,333,755 B2 | 12/2012 | Cooper et al. | |
| 8,348,931 B2 | 1/2013 | Cooper et al. | |
| 8,444,631 B2 | 5/2013 | Yeung et al. | |
| 8,479,969 B2 | 7/2013 | Shelton et al. | |
| 8,506,555 B2 | 8/2013 | Ruiz | |
| 8,551,115 B2 * | 10/2013 | Steger | A61B 34/30 606/1 |

(Continued)

FOREIGN PATENT DOCUMENTS

CN 1127332 A 7/1996
CN 2573759 Y 9/2003

(Continued)

OTHER PUBLICATIONS

Office Action dated Jun. 22, 2017 for Japanese Application No. 2016177316 filed Sep. 12, 2016, 7 pages.

(Continued)

*Primary Examiner* — Ahmed M Farah

(57) ABSTRACT

A mechanical interface for a robotic medical instrument permits engagement of the instrument and a drive system without causing movement of an actuated portion of the instrument. An instrument interface can include a symmetrical, tapered or cylindrical projection on one of a medical instrument or a drive system and a complementary bore in the other of the drive system or the medical instrument. Symmetry of the projection and the bore allows the projection to be compression fit to the bore regardless of the rotation angle of the drive system relative to the medical instrument.

17 Claims, 4 Drawing Sheets

(56) References Cited

U.S. PATENT DOCUMENTS

| | | | |
|---|---|---|---|
| 8,644,988 B2 * | 2/2014 | Prisco | A61B 34/71 600/146 |
| 8,771,270 B2 | 7/2014 | Burbank | |
| 8,800,838 B2 | 8/2014 | Shelton et al. | |
| 8,911,471 B2 | 12/2014 | Spivey et al. | |
| 9,028,494 B2 | 5/2015 | Shelton et al. | |
| 9,078,684 B2 | 7/2015 | Williams | |
| 9,121,494 B2 | 9/2015 | Buchleitner | |
| 9,204,923 B2 | 12/2015 | Manzo et al. | |
| 9,232,979 B2 | 1/2016 | Parihar et al. | |
| 9,259,274 B2 * | 2/2016 | Prisco | B25J 9/1045 |
| 9,291,793 B2 | 3/2016 | Cooper | |
| 9,339,342 B2 | 5/2016 | Prisco et al. | |
| 9,533,122 B2 | 1/2017 | Weitzner et al. | |
| 9,687,312 B2 | 6/2017 | Dachs, II et al. | |
| 9,757,149 B2 | 9/2017 | Cooper et al. | |
| 1,001,624 A1 | 7/2018 | Cooper et al. | |
| 1,002,219 A1 | 7/2018 | Cooper et al. | |
| 10,022,194 B2 * | 7/2018 | Prisco | B25J 9/1045 |
| 10,130,366 B2 * | 11/2018 | Shelton, IV | A61B 17/105 |
| 2002/0087048 A1 | 7/2002 | Brock et al. | |
| 2002/0096885 A1 | 7/2002 | Gomez et al. | |
| 2002/0111635 A1 | 8/2002 | Jensen et al. | |
| 2002/0153221 A1 | 10/2002 | Schnepf | |
| 2004/0035243 A1 | 2/2004 | Duval | |
| 2005/0277875 A1 | 12/2005 | Selkee | |
| 2006/0084945 A1 | 4/2006 | Moll et al. | |
| 2007/0137371 A1 | 6/2007 | Devengenzo et al. | |
| 2007/0156019 A1 | 7/2007 | Larkin et al. | |
| 2007/0156122 A1 | 7/2007 | Cooper et al. | |
| 2007/0232858 A1 | 10/2007 | Macnamara et al. | |
| 2007/0287992 A1 | 12/2007 | Diolaiti et al. | |
| 2008/0046122 A1 | 2/2008 | Manzo et al. | |
| 2008/0065102 A1 | 3/2008 | Cooper | |
| 2008/0087871 A1 | 4/2008 | Schena | |
| 2008/0103491 A1 | 5/2008 | Omori et al. | |
| 2008/0196533 A1 | 8/2008 | Bergamasco et al. | |
| 2009/0000899 A1 | 1/2009 | Paterra et al. | |
| 2009/0062813 A1 * | 3/2009 | Prisco | A61B 34/30 606/130 |
| 2009/0088774 A1 | 4/2009 | Swarup et al. | |
| 2009/0324161 A1 | 12/2009 | Prisco | |
| 2010/0011900 A1 | 1/2010 | Burbank | |
| 2010/0170519 A1 | 7/2010 | Romo et al. | |
| 2010/0175701 A1 | 7/2010 | Reis et al. | |
| 2010/0318101 A1 | 12/2010 | Choi | |
| 2011/0015650 A1 | 1/2011 | Choi et al. | |
| 2011/0118754 A1 | 5/2011 | Dachs, II et al. | |
| 2011/0160743 A1 | 6/2011 | Espinal | |
| 2011/0213383 A1 | 9/2011 | Lee et al. | |
| 2011/0277775 A1 | 11/2011 | Holop et al. | |
| 2011/0282356 A1 | 11/2011 | Solomon et al. | |
| 2011/0282357 A1 | 11/2011 | Rogers et al. | |
| 2011/0282359 A1 * | 11/2011 | Duval | A61B 17/3423 606/130 |
| 2011/0295269 A1 | 12/2011 | Swensgard et al. | |
| 2011/0295270 A1 | 12/2011 | Giordano et al. | |
| 2012/0021867 A1 | 1/2012 | Rosmarin | |
| 2012/0111136 A1 | 5/2012 | Kawakami | |
| 2012/0118917 A1 | 5/2012 | Naughton et al. | |
| 2012/0123441 A1 | 5/2012 | Au et al. | |
| 2012/0239060 A1 | 9/2012 | Orban, III | |
| 2012/0245596 A1 | 9/2012 | Meenink et al. | |
| 2012/0289974 A1 * | 11/2012 | Rogers | A61B 34/71 606/130 |
| 2013/0331857 A9 | 12/2013 | Prisco et al. | |
| 2014/0005678 A1 | 1/2014 | Shelton et al. | |
| 2014/0100558 A1 | 4/2014 | Schmitz et al. | |
| 2015/0008090 A1 | 1/2015 | Adamczak et al. | |
| 2015/0150635 A1 | 6/2015 | Kilroy et al. | |
| 2015/0157355 A1 | 6/2015 | Price et al. | |
| 2016/0166342 A1 | 6/2016 | Prisco | |
| 2016/0184034 A1 | 6/2016 | Holop et al. | |
| 2016/0184036 A1 | 6/2016 | Solomon et al. | |
| 2016/0184037 A1 | 6/2016 | Cooper et al. | |
| 2016/0199138 A1 | 7/2016 | Cooper et al. | |
| 2016/0361049 A1 | 12/2016 | Dachs, II et al. | |
| 2017/0165017 A1 | 6/2017 | Chaplin et al. | |
| 2018/0311001 A1 | 11/2018 | Prisco et al. | |

FOREIGN PATENT DOCUMENTS

| | | |
|---|---|---|
| CN | 2626684 Y | 7/2004 |
| CN | 1650117 A | 8/2005 |
| CN | 1763638 A | 4/2006 |
| CN | 102014759 A | 4/2011 |
| JP | H06114000 A | 4/1994 |
| JP | H10249777 A | 9/1998 |
| JP | 2002200091 A | 7/2002 |
| JP | 2003024336 A | 1/2003 |
| JP | 2004105451 A | 4/2004 |
| JP | 2005288590 A | 10/2005 |
| JP | 2006061364 A | 3/2006 |
| JP | 2008104854 A | 5/2008 |
| JP | 2010220955 A | 10/2010 |
| JP | 2012504016 A | 2/2012 |
| WO | WO-9729690 A1 | 8/1997 |
| WO | WO-2005039835 A1 | 5/2005 |
| WO | WO-2007075864 A1 | 7/2007 |
| WO | WO-2007136783 A2 | 11/2007 |
| WO | WO-2010039387 A1 | 4/2010 |
| WO | WO-2011037394 A2 | 3/2011 |
| WO | WO-2015142290 A1 | 9/2015 |

OTHER PUBLICATIONS

Office Action dated Nov. 30, 2016 for Chinese Application No. 201510185999.6 filed Sep. 2, 2009, 24 pages.

Extended European Search Report for Application No. EP18184785.6, dated Nov. 23, 2018, 6 pages.

International Search Report and Written Opinion for Application No. PCT/US14/050838, dated Nov. 25, 2014, 11 pages.

International Search Report and Written Opinion for Application No. PCT/US14/50957, dated Nov. 21, 2014, 11 pages.

International Search Report and Written Opinion for Application No. PCT/US14/51001, dated Nov. 20, 2014, 11 pages.

International Search Report and Written Opinion for Application No. PCT/US14/51074, dated Nov. 20, 2014, 13 pages.

International Search Report and Written Opinion for Application No. PCT/US2014/051033, dated Nov. 19, 2014, 9 pages.

International Search Report and Written Opinion for Application No. PCT/US2014/051050, dated Nov. 25, 2014, 14 pages.

Extended European Search Report for Application No. 14836283.3, dated Sep. 4, 2017, 11 pages.

Extended European Search Report for Application No. 14836336.9, dated Jun. 16, 2017, 9 pages.

Extended European Search Report for Application No. 14836512.5, dated Aug. 3, 2017, 13 pages.

Extended European Search Report for Application No. 14836696.6, dated Jun. 16, 2017, 9 pages.

Extended European Search Report for Application No. 14836832.7, dated Jun. 9, 2017, 8 pages.

Extended European Search Report for Application No. EP14836874.9, dated Mar. 17, 2017, 10 pages.

Partial Supplementary European Search Report for Application No. EP14836283.3, dated May 17, 2017, 12 pages.

International Search Report and Written Opinion for Application No. PCT/US2012/037269, dated Sep. 19, 2012, 10 pages.

Office Action dated Dec. 26, 2014 for Japanese Application No. 20140021913 filed Feb. 7, 2008, 10 pages.

Office Action dated Sep. 30, 2015 for Japanese Application No. 20140021913 filed Feb. 7, 2008, 7 pages.

PCT/US09/55727 International Search Report and Written Opinion of the International Searching Authority, dated Feb. 3, 2010, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(56) References Cited

OTHER PUBLICATIONS

Final Action dated Apr. 8, 2019 for Korean Application No. 10-2013-7032821 filed May 10, 2012, 11 pages.
Office Action dated Sep. 7, 2018 for Korean Application No. 10-2013-7032821 filed May 10, 2012, 16 pages.
Decision of Final Rejection for Korean App. No. 10-2013-7032821, dated Jul. 3, 2019.
Notice of Dismissal of Amendment for Korean App. No. 10-2013-7032821, dated Jul. 3, 2019.

* cited by examiner

MEDICAL INSTRUMENT ENGAGEMENT PROCESS

CROSS-REFERENCE TO RELATED APPLICATIONS

This patent document is a divisional and claims benefit of the earlier filing date of U.S. patent application Ser. No. 13/360,395, filed Jan. 27, 2012, now U.S. Pat. No. 9,339,342, which claims the priority of U.S. Provisional Pat. App. No. 61/485,702, filed May 13, 2011 and which is a continuation-in-part of U.S. patent application Ser. No. 12/286,644, filed Sep. 30, 2008, now U.S. Pat. No. 9,259,274, all of which are hereby incorporated by reference in their entirety.

BACKGROUND

Robotically controlled systems such as employed for minimally invasive medical procedures can include large and complex equipment to precisely control and drive relatively small tools or instruments. (As used herein, the terms "robot" or "robotically" and the like include teleoperation or telerobotic aspects.) FIG. 1A illustrates an example of a known robotically controlled system 100. System 100, which may, for example, be part of a da Vinci® Surgical System available from Intuitive Surgical, Inc., includes a patient-side cart 110 having multiple arms 130. Each arm 130 has a docking port 140 that generally includes a drive system with a mechanical interface for mounting and providing mechanical power for operation of an instrument 150. Arms 130 can be used during a medical procedure to move and position respective medical instruments 150 for the procedure.

FIG. 1B shows a bottom view of a known instrument 150. Instrument 150 generally includes a transmission or backend mechanism 152, a main tube 154 extending from the backend mechanism 152, and a functional tip 156 at the distal end of the main tube 154. Tip 156 generally includes a medical tool such as a scalpel, scissors, forceps, or a cauterizing instrument that can be used during a medical procedure. Drive cables or tendons 155 connect to tip 156 and extend through main tube 154 to backend mechanism 152. Backend mechanism 152 typically provides a mechanical coupling between the drive tendons of the instrument 150 and motorized axes of the mechanical interface of a drive system 140. In particular, gears or disks 153 having features such as projections or holes that are positioned, sized, and shaped to engage complementary features on the mechanical interface of a drive system 140. In a typical instrument, rotation of disks 153 pulls on respective tendons 155 and actuates corresponding mechanical links in tip 156. System 100 can thus control movement and tension in drive tendons 155 as needed to position, orient, and operate tip 156. Further details of known surgical systems are described, for example, in U.S. Pat. No. 7,048,745 to Tierney et al., entitled "Surgical Robotic Tools, Data Architecture, and Use," which is hereby incorporated by reference in its entirety.

Instruments 150 of system 100 can be interchanged by removing one instrument 150 from a drive system 140 and then installing another instrument 150 in place of the instrument removed. The installation process in general requires that the features on disks 153 properly engage complementary features of the drive system 140. However, before installation, the orientations of disks 153 on instrument 150 are generally unknown to patient-side cart 110. Further, equipment such patient-side cart 110 is often covered for a medical procedure by a sterile barrier because of the difficulty in cleaning and sterilizing complex equipment between medical procedures. These sterile barriers can include a sterile adaptor (not shown) that is interposed between docking port 140 and instrument backend 152. For example, above referenced U.S. Pat. Nos. 7,048,745 and 7,699,855 to Anderson et al., entitled "Sterile Surgical Adaptor", which is hereby incorporated by reference in its entirety, describe some exemplary sterile barrier and adaptor systems.

A typical installation process for an instrument 150 involves mounting backend mechanism 152 without regard for the orientations of disks 153 on a drive system 140, possibly with an intervening sterile adaptor. The drive motors in drive system 140 may be then be rotated back and forth multiple times during the installation procedure to ensure that the complementary features mesh with and securely engage each other for operation of the newly installed instrument 150. At some point during the installation process, the drive motors become securely engaged to rotate respective disks 153. However, the instrument 150 being installed may move in an unpredictable manner at times during the installation procedure because the drive motors positively engage respective disks 153 of instrument 150 at different and unpredictable times. Such unpredictable motion is unacceptable when an instrument is inserted in a patient. In general, clear space is required around an instrument 150 to accommodate random movements of the instrument tip during an installation procedure.

SUMMARY

In accordance with an aspect of the invention, a mechanical interface for a robotic medical instrument permits engagement of the instrument and a drive system without causing movement of the tip of the instrument. Accordingly, an instrument can be engaged with the drive system in a patient-side cart after the instrument is manually posed in a desired configuration or even after the instrument has been inserted for a medical procedure. This permits manual insertion of an instrument followed by robotic control of the instrument.

In one embodiment, an instrument interface includes a symmetrical, tapered or cylindrical projection on one of a medical instrument and a drive system (potentially including a sterile barrier) and a complementary bore in the other of the drive system or the instrument. With cylindrical projection and bore, the diameter of the bore can contract, for example, using the tension in a tendon wrapped around the mechanical element containing the bore, to reduce the diameter of the bore and provide the instrument with frictional forces sufficient to transmit driving torque to the medical instrument. In any case, symmetry of the projection and the bore allows the projection to be compression fit into the bore regardless of the rotation angle of the drive system relative to the instrument.

In one specific embodiment of the invention, a system includes a medical instrument and a drive system. The medical instrument includes a rotatable element that when rotated actuates the medical instrument. The drive system has an interface configured to releasably engage the medical instrument, and a first feature of the rotatable element and a second feature of the interface are shaped to engage each other without inducing rotation that actuates the medical instrument.

Another embodiment of the invention is a medical instrument. The medical instrument includes an actuated structure and a mechanical element connected so that rotation of the mechanical element actuates the actuated structure. The mechanical element has an engagement feature shaped such that for any pose of the actuated structure, the engagement feature can engage a complementary engagement feature on a drive system without inducing rotation that actuates the actuated structure.

Yet another embodiment of the invention is a drive system for a medical instrument. The drive system includes a motor; and an interface coupled to the motor and configured to releasably engage the medical instrument so that rotation of the motor actuates the medical instrument. The interface includes an engagement feature shaped such that for any pose of the medical instrument, the engagement feature can engage a complementary engagement feature of the medical instrument without inducing rotation that actuates the medical instrument.

Still another embodiment of the invention is a method for engaging a medical instrument and a drive system. The method includes bringing a first feature on a rotatable element of the medical instrument into contact with a second feature on a drive element of the drive system without rotating either of the elements. An engagement force is then applied to create friction between the rotatable element and the drive element without rotating either of the elements. When thus engaged, the drive system can be operated to actuate the medical instrument, and the friction transfers torque that the drive system applies to the first rotatable element to the second rotatable element and thereby actuates the mechanical instrument.

BRIEF DESCRIPTION OF THE DRAWINGS

Use of the same reference symbols in different figures indicates similar or identical items.

DETAILED DESCRIPTION

In accordance with an aspect of the invention, a medical instrument can be installed on and engaged with a drive system without actuating or otherwise moving the joints or tip of the instrument. Engagement without actuation can be implemented using symmetric mechanical elements that securely engage through compression or friction to maintain the relative orientation of a drive mechanism and the mechanical interface of the instrument. In one embodiment, a symmetric tapered shaft of a drive system or a backend mechanism fits into a symmetric tapered bore or slot in a mechanical element of the backend mechanism or drive system, and friction maintains the orientation of the shaft and the slotted mechanical element. In another specific embodiment, a symmetric shaft can be inserted into a mechanical element containing a bore that contracts in diameter to securely hold the relative orientation of the shaft and the mechanical element. For example, a shaft of a drive motor can fit into a bore within a capstan that is sufficiently flexible that tension in a tendon wrapped around the capstan causes the bore to collapse onto the shaft. The ability to install an instrument without actuating the instrument allows posing of the instrument in a desired configuration before the instrument is installed on a drive system and allows installation of an instrument after the instrument has been inserted into a cannula or even into a patient.

Figure 1A:
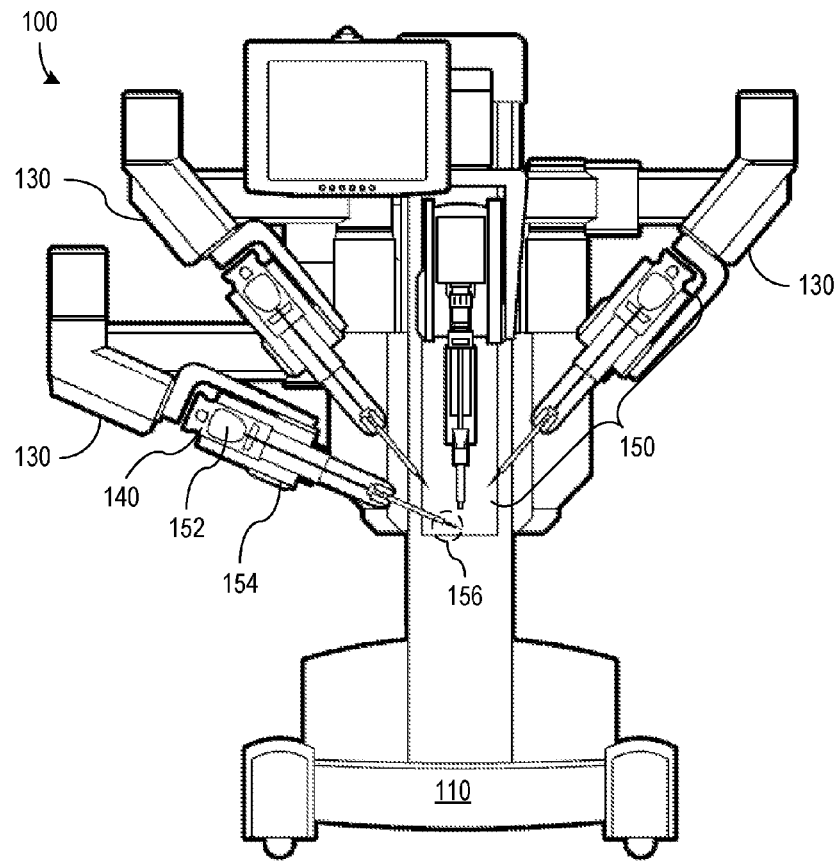
FIG. 1A shows a patient-side cart of a robotically controlled system that may employ a medical instrument in accordance with an embodiment of the invention.
Figure 1B:
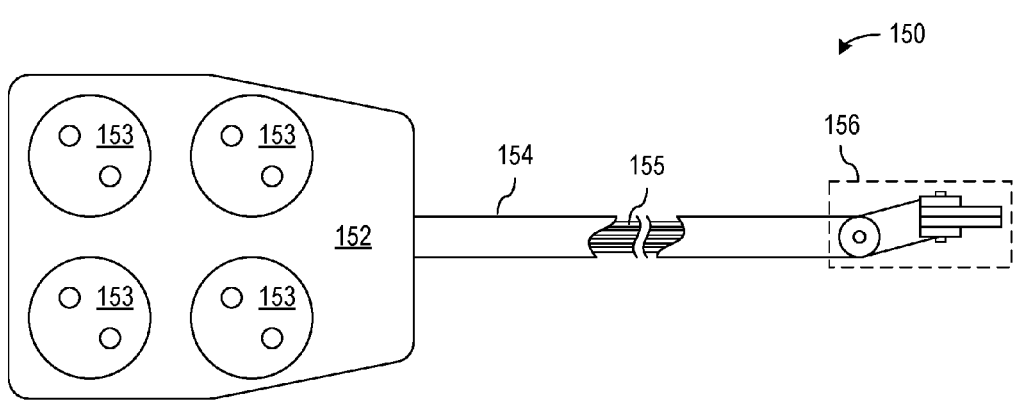
FIG. 1B shows a bottom view of a known medical instrument employing drive gears or disks that require rotation for alignment with a drive motor.
Figure 2:
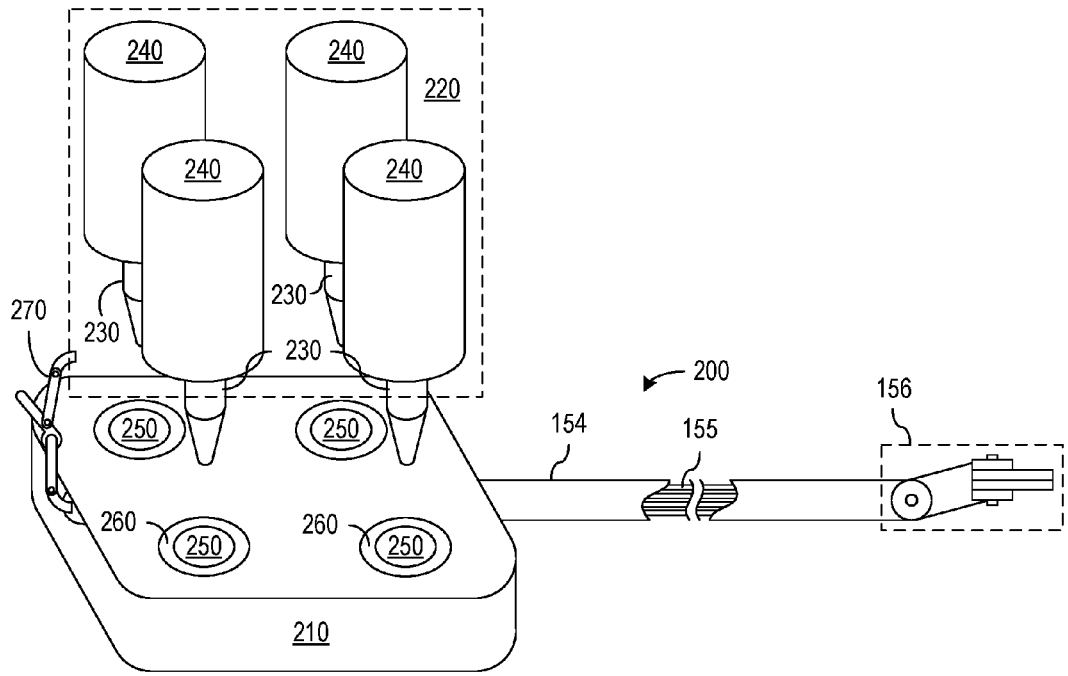
FIG. 2 shows an embodiment of the invention in which an instrument can engage a set of drive motors without movement or actuation of the working tip of the instrument.

FIG. 2 illustrates an embodiment of the invention in which a medical instrument 200 has a backend mechanism 210 that mounts on a drive system 220 having one or more tapered drive shafts 230. Drive system 220 may be part of a docking port or a tool holder of a medical system such as the patient-side cart 110 of FIG. 1, which allows instrument 200 to be installed or removed for different medical procedures or during a medical procedure. Tapered shafts 230 can be the shafts of drive motors 240 of drive system 220 or can be separate elements that attach to the motor shafts and transmit motor rotation to backend mechanism 210 for movement of a jointed section of instrument 200, e.g., an instrument tip 156. In general, instrument tip 156 can be of any desired type but is illustrated in FIG. 2 as being on the distal end of a main shaft 154 through which tendons 155 extend and connect to tip 156. Backend mechanism 210 generally contains a transmission mechanism (not shown) that converts the rotation of motors 240 into movement of tendons 155 which operate the joints of instrument 200 including joints in tip 156.

Tapered shafts 230 can be simple, low cost, and robust mechanical elements that are precisely machined using conventional techniques to produce a tapered shape with a circular cross-section. Many types of tapers could be employed on tapered shafts 230. For example, Morse tapers with or without an end tang or guide could be used. Tapered shafts 230 are free to spin on their axis and are symmetric about their respective rotation axes, i.e., have circular cross-sections.

Figure 3:
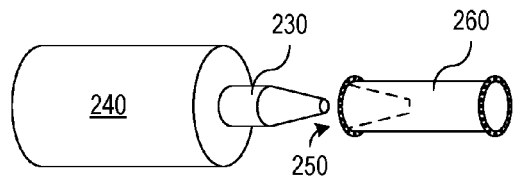
FIG. 3 shows a drive motor and a mechanical element of a backend mechanism in accordance with an embodiment of the invention in which the drive motor can engage the backend mechanism without turning of the mechanical element.

Each tapered shaft 220 is further shaped to fit into a complementary tapered hole 250 or slot in a mechanical element 260 of backend mechanism 210. Mechanical element 260 may be, for example, a hollowed-out spindle having a tapered hole 250 that matches the shape of the corresponding tapered shaft 230 and in particular has circular cross-sections matching those of tapered shafts 220. More generally, tapered holes 250 can be formed in any mechanical elements 260 of instrument backend 210 that are free to spin on their axis, where a mechanical transmission system of backend mechanism 210 converts the rotations of the slotted mechanical elements 260 into movements of tendons 155 and instrument tip 156. For example, FIG. 3 shows how a tapered shaft 230 of a motor 240 directly fits into a tapered hole or bore 250 in a capstan 260. In one specific embodiment, tapered holes 250 are formed in capstans that transmit the motion to tendons 155 as described in U.S. Pat. App. Pub. No. 2010/0082041, entitled "Passive Preload and Capstan Drive for Surgical Instruments," which is hereby incorporated by reference in its entirety. More generally, a capstan is just one example of a mechanical element 260 that may be employed within backend mechanism 210 to convert motor rotation into tendon movement and instrument actuation.

Figure 4:
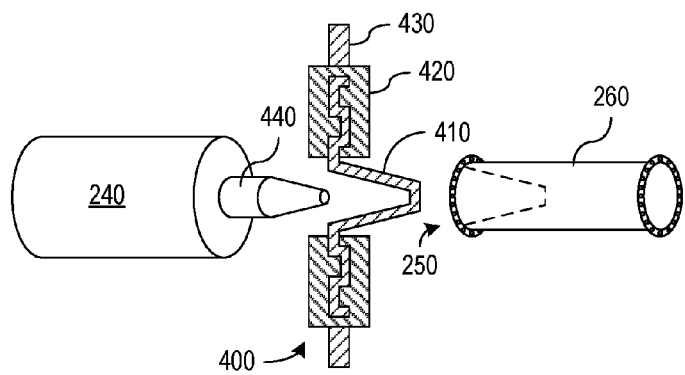
FIG. 4 illustrates an embodiment of the invention in which a portion of a sterile adaptor is interposed between a drive motor and a mechanical element of the backend mechanism of a medical instrument.

FIG. 4 schematically illustrates how a sterile adaptor 400 in a sterile barrier can be interposed between a drive element 440 and a mechanical element 260 that is rotatable to actuate a medical instrument. In the illustrated configuration, sterile adaptor 400 includes an element 410 that is free to rotate in a circumferential bearing 420 that maintains a sterile barrier by means of a labyrinth seal that performs the desired medical function while allowing element 410 to rotate about an axis corresponding to the rotation axis of drive element 440 and rotatable element 260. Element 410 may be, for example, of a layer of a mechanically resistant plastic about 0.5 to 2 mm thick that is molded to be interposed between drive element 440 and a hole 250 in rotatable element 260. In particular, element 410 in FIG. 4 is shaped to receive drive element 440 on the manipulator side and to have a projection that fits into tapered hole 250 in rotatable element 260 that is part of the backend mechanism of a medical instrument. A sterile sheet 430 or other portions of the sterile barrier can be connected to bearing 420 to maintain surgical field sterility. FIG. 4 illustrates features of a sterile adaptor in a schematic fashion to illustrate general working principles relevant to the present invention. U.S. Pat. Nos. 7,048,745 and 7,699,855, which are incorporated by reference above, provide additional description of the features of some sterile adaptors for medical instruments.

FIG. 4 also shows an embodiment of the invention in which drive element 440 has a tapered shape that can engage barrier element 410 without rotation. Alternatively, drive element 440 could have a keyed or rough surface, and barrier element could be smooth but sufficiently compliant to be forced onto drive element 440. In yet another alternative embodiment, drive element 440 has a keyed engagement feature with projections or indentations that engage complementary features of barrier element 410. With keyed features on drive element 440 and the manipulator side of barrier element 410, rotation of drive element 440 or barrier element 410 may be necessary in order to align the keyed features when the sterile barrier is fitted to a manipulator. However, the sterile barrier can be fitted to the manipulator once for a medical procedure and is fitted before any medical instruments are engaged on the manipulator. Rotation of drive element 440, barrier element 410, or rotatable element 260 is not required when engaging an instrument on the drive system because the instrument side of barrier element 410 has a surface shaped to fit bore 250 without any rotation.

Instrument engagement using the system of FIG. 2 can be performed by slipping the holes 240 in instrument backend 210 onto tapered shafts 230 of docking port 220, with or without an interposed sterile adapter. A latch or other mechanism 270 can be used to provide an engagement force that presses backend mechanism 210 onto docking port 220 and drives tapered shafts 230 into tapered holes 250. The shapes of shafts 230 and holes 250 automatically accommodate some initial misalignment between instrument 200 and drive system 220 since the tapers guide shafts 230 and holes 250 into the desired relative positions. Additional misalignment between backend mechanism 210 and docking port 220 or relative misalignment or spacing variation of the drive axes of backend mechanism 210 or docking port 220 can be accommodated using flexible mountings for tapered shafts 230 or slotted elements 260 as described further below. When engaged and held in place, compression and the friction across the entire surface of each tapered shaft 230 contacting the matching inner surface of a corresponding hole 240 can provide a large amount of torque transmission, so that keys or gear teeth are not required to transfer torque or rotational movement from drive system 220 to backend mechanism 210. Further, no rotation of motors 240 or slotted mechanical elements 260 of backend mechanism 210 is required during the engagement procedure. Also, the instrument can be engaged while having any desired configuration of slotted elements 260 and any pose of tip 156, and instrument tip 156 does not move during engagement. The lack of tip movement makes the engagement process possible while tip 156 is inserted in a cannula or even at an operating site within a patient.

Control of medical instrument 200 after engagement of backend mechanism 210 and drive system 220 can be based on a measurement of the pose (e.g., the positions of joints) of medical instrument 210 and measurements of the rotation angles of each of motors 240. Alternatively, a control process using differences between measured and desired instrument pose or configuration could be employed. U.S. patent application Ser. No. 12/945,734, entitled, "Tension Control in Actuation of Multi-Joint Medical Instruments" and U.S. patent application Ser. No. 12/780,417, entitled "Drive Force Control in Medical Instrument Providing Position Measurements" describe exemplary systems for control of medical instruments and are hereby incorporated by reference in their entirety.

Figure 5:
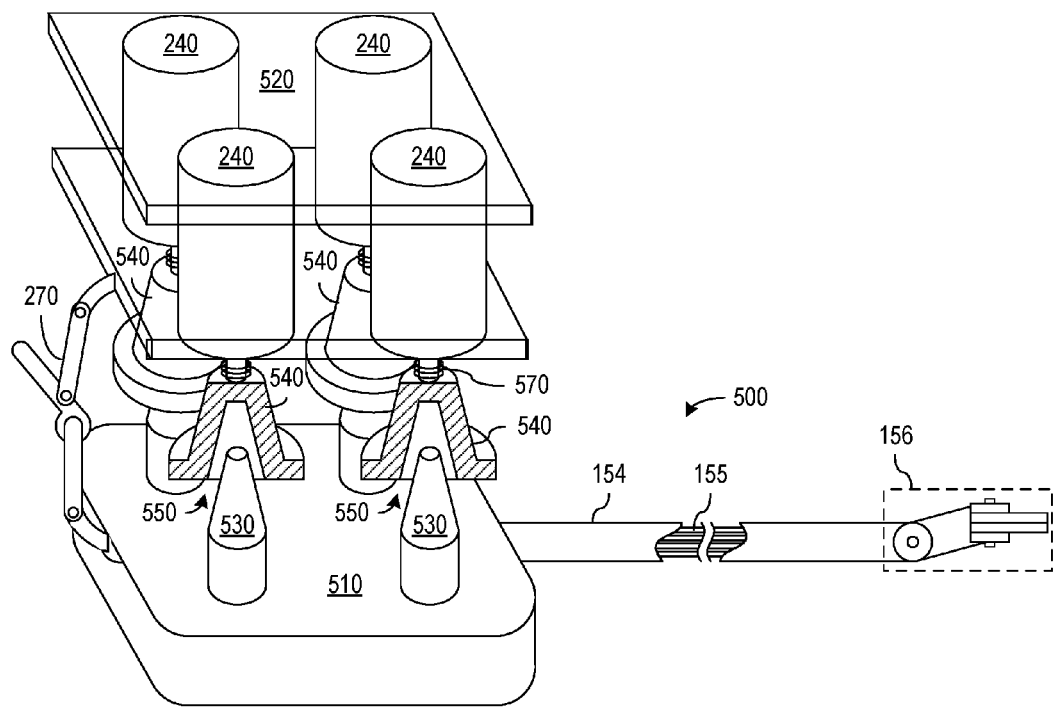
FIG. 5 shows an embodiment of the invention in which a medical instrument has tapered projections that can engage drive motors without movement or actuation of the tip of the medical instrument.

FIG. 2 illustrates a system in which drive system 220 includes one or more tapered shafts 230 and instrument backend 210 includes complementary tapered holes 230. FIG. 5 illustrates a system in accordance with an alternative embodiment in which tapered shafts 530 extend from a backend mechanism 510 of a medical instrument 500 and are rotated to operate the transmission within backend mechanism 510 and actuate or move joints of instrument 500. In this configuration, motors 240 in a drive system 520 have shafts with fixtures 540 shaped to provide tapered holes 550 that are complementary to the shape of tapered shafts 530 or an interposed portion of a sterile adaptor. Other than the reversing of the positions of the tapered shafts and the tapered holes, backend mechanism 510 and instrument holder 520 of system 500 can be engaged and operated in the same manner as backend mechanism 210 and instrument holder 220 of system 200, which is described above with reference to FIG. 2. As described above, a docking system can attach medical instrument 500 to drive system 520 and apply an engagement force so that the friction between features 530 and 540 is sufficient to transmit the torque required for operation of medical instrument 500. The docking system could include, for example, a latch 270 and a spring preload 570.

Figure 6:
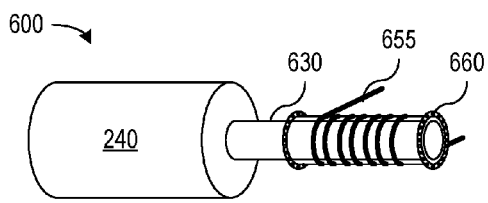
FIG. 6 shows an embodiment of the invention that uses compression caused by a tendon wrapped around a capstan to contract a bore in the capstan and engage a drive motor.

In accordance with another aspect of the invention, a motor in a drive system can operate a mechanical element of a backend mechanism through a frictional engagement created by radial compression of a hole or bore in a mechanical element. FIG. 6, for example, illustrates a system 600 including a motor 240 having a cylindrical shaft 630 that fits within a cylindrical bore in a mechanical element 660 of a backend mechanism such as backend mechanism 210 of FIG. 2. Mechanical element 660 is a capstan, and a drive tendon 655, which may attach to an articulated joint of the instrument, is wound around capstan 660. Tendon 655 can be a cable, a wire, a filament, or similar structure that is able to wrap around capstan 660 and may be made of metal or a synthetic material. Capstan 660 is radially flexible so that the application of tension in tendon 655 causes the diameter of the bore in capstan 660 to decrease, thereby clamping capstan 660 onto shaft 630 with or without an intervening, substantially cylindrical plastic component of a sterile barrier (not shown). One more surface of the sterile barrier component, capstan 660, or shaft 630 may include splines, teeth, or other features to improve the traction and torque transmission capability of the engagement, provided that the other surface of the sterile adaptor can engage the contoured surface without rotation. However, meshing of the splines or teeth of two surfaces generally requires rotation of shaft 630 and capstan 660, which may be undesirable.

The process of engaging the instrument on a drive system including motor 240 may further begin with tendon 655 being sufficiently relaxed so that shaft 630 (with or without an interposed portion of a sterile barrier) can slide into the bore of mechanical element 660, without any rotation of mechanical element 660. Shaft 630 and the bore of mechanical element 660 can be symmetrical (e.g., have a circular cross-section) so that shaft 630 can be inserted into mechanical element 660 regardless of the relative orientation of shaft 630 and mechanical element 660. A mechanism within the backend mechanism can then increase or apply the pre-tension to tendon 655 to cause the wraps of tendon 655 to clamp flexible mechanical element 660 on shaft 630. For example, displacing a capstan in a proximal direction relative to the body of an instrument can increase the tension in both ends of a tendon extending from the capstan, causing opposing torques on a joint coupled to the ends of tendon 655. As a result, no joint movement occurs when the tension is increased. Alternatively, when only one end of tendon 655 attaches to an articulated joint, pre-tension in tendon 655 can be preset to permit insertion of shaft 630 (with at least one smooth, cylindrical interface between the capstan, sterile barrier, and input shaft) into capstan 660, so that capstan 660 couples more strongly to shaft 630 when driven in a direction that increases tension in tendon 655. Capstan 660 may then be permitted to slip relative to shaft 630 when driven in the reverse direction.

Figure 7:
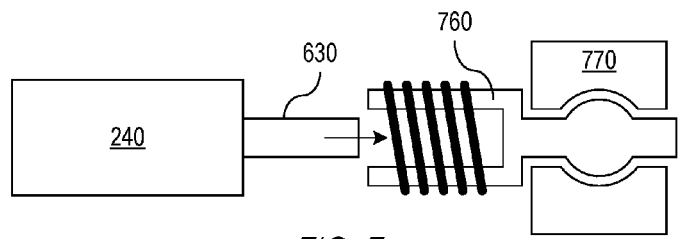
FIG. 7 illustrates an embodiment of the invention employing a floating or loose shaft to accommodate misalignment between a drive mechanism and a medical instrument.
Figure 8:
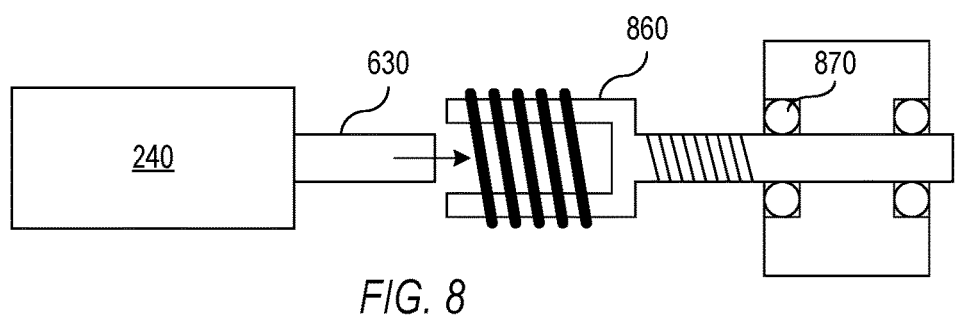
FIG. 8 illustrates an embodiment of the invention employing a flexible shaft to accommodate misalignment between a drive mechanism and a medical instrument.

Motor shaft 630 and the bore of mechanical element 660 do not have tapering that accommodates misalignment in the same manner as embodiments of the invention using tapered shafts and holes. However, compliance can be provided in shaft 630 or capstan 660 to accommodate initial misalignment of motor 240 and capstan 660 during an engagement process. FIG. 7, for example, shows an embodiment of the invention in which a capstan 760 is loosely retained in a structure 770 of the backend mechanism in such a way that capstan 760 can move into alignment with shaft 530 and then be supported primarily by shaft 630 and the bearings of motor 240 when capstan 760 is engaged with motor 630. Alternatively, as shown in FIG. 8, a capstan 860 may be supported by bearings 870 in the backend mechanism of an instrument but incorporate a flexure, e.g., a spring or helical structure, to allow movement for alignment of shaft 630 and capstan 860. The compliance of the mountings shown in FIGS. 7 and 8 can accommodate misalignment of a drive element in a drive system and a corresponding rotatable element in a medical instrument and accommodate differences in the spacing or orientation of multiple drive elements in a drive system relative to the corresponding rotatable elements in a medical instrument.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A method for operating a medical instrument and a drive system, the medical instrument comprising at least one component, comprising:
   bringing a first feature on a rotatable element of the medical instrument into contact with a second feature on a drive element of the drive system without restricting a rotation angle of the first feature relative to the second feature, the second feature being shaped to engage the first feature, and the medical instrument including a mechanism coupled to the rotatable element and coupled to actuate the at least one component of the medical instrument in response to rotation of the rotatable element;
   applying an engagement force to create friction between the first and second features, wherein bringing the first feature into contact with the second feature and applying the engagement force engages the first and the second features without inducing rotation that actuates the medical instrument; and
   operating the drive system to rotate the drive element and the rotatable element, wherein the friction transfers torque that the drive element applies to the rotatable element to rotate the rotatable element and thereby to actuate the component.

2. The method of claim 1, further comprising determining a pose of the medical instrument after engaging the medical instrument and the drive system.

3. The method of claim 1, wherein:
   one of the first and second features comprises a tapered projection;
   another of the first and second features comprise a tapered hole in which the tapered projection fits; and
   applying the engagement force comprises pressing the tapered projection into the tapered hole.

4. The method of claim 1, wherein:
   one of the first and second features comprises a bore in a capstan around which a tendon is wrapped;
   another of the first and second features fits within the bore; and
   applying the engagement force comprises applying tension to the tendon so that a diameter of the bore decreases.

5. The method of claim 1, wherein the second feature is part of an adaptor in a sterile barrier.

6. The method of claim 1, further comprising determining a pose of the medical instrument after applying the engagement force.

7. The method of claim 1, wherein at least one of the first feature or the second feature is compliant to accommodate misalignment during engagement.

8. The method of claim 1, wherein applying the engagement force comprises engaging a latch to press the first feature toward the second feature.

9. A method for engaging a medical instrument and a drive system, wherein the medical instrument comprises a first interface that includes a plurality of first elements, each of the first elements including a first feature that is rotatable to actuate a component of the medical instrument, and wherein the drive system comprises a second interface that includes a plurality of drive elements, each of the drive elements including a second feature shaped to engage a corresponding one of the first elements, the method comprising:

bringing the first interface into contact with the second interface without restricting rotation angles of the first features relative to the second features;

applying an engagement force to create friction between the first and second features, wherein bringing the first interface into contact with the second interface and applying the engagement force engages the first and the second features without inducing rotation that actuates the medical instrument; and operating the drive system to actuate the components of the medical instrument, wherein the friction transfers torques that the drive elements apply to the first features to actuate the components of the medical instrument.

10. The method of claim 9, wherein each of the drive elements comprises a drive motor, and each of the second features comprises a portion of an adaptor in a sterile barrier that is between the drive motors and the medical instrument.

11. The method of claim 9, wherein:
bringing the first interface into contact with the second interface comprises inserting tapered projections that correspond to one of the first features and the second features into tapered holes that are in the other of the first features and the second features; and
applying the engagement force comprises pressing the tapered projections into the tapered holes.

12. The method of claim 9, wherein:
bringing the first interface into contact with the second interface comprises inserting a plurality of projections that correspond to one of the first features and the second features into bores in a plurality of capstans that correspond to the other of the first features and the second features; and
applying the engagement force comprises applying tensions to tendons wrapped around the capstans so that each of the bores decreases in diameter.

13. The method of claim 12, wherein at least one capstan of the plurality of capstans includes a flexure structure to accommodate misalignment during engagement of the at least one capstan with a corresponding projection of the plurality of projections.

14. The method of claim 12, wherein at least one capstan of the plurality of capstans is loosely retained in the other of the first features and the second features to accommodate misalignment during engagement with a corresponding projection of the plurality of projections.

15. The method of claim 9, further comprising determining a pose of the medical instrument after applying the engagement force.

16. The method of claim 9, wherein at least one of the first elements or the second elements is compliant to accommodate misalignment during engagement.

17. The method of claim 9, wherein applying the engagement force comprises engaging a latch to press the first features toward the second features.

* * * * *